(12) United States Patent
Hu et al.

(10) Patent No.: US 10,988,503 B1
(45) Date of Patent: Apr. 27, 2021

(54) SIX-MEMBERED RING-CONTAINING NUCLEOSIDE COMPOUND AND PREPARATION METHOD THEREOF

(71) Applicant: NANTONG WEISHUN BIOTECHNOLOGY CO., LTD, Nantong (CN)

(72) Inventors: Min Hu, Nantong (CN); Dongchun Hong, Nantong (CN); Weimin Xue, Nantong (CN)

(*) Notice: Subject to any disclaimer, the term of this patent is extended or adjusted under 35 U.S.C. 154(b) by 0 days.

(21) Appl. No.: 16/924,239

(22) Filed: Jul. 9, 2020

Related U.S. Application Data

(63) Continuation of application No. PCT/CN2020/088682, filed on May 6, 2020.

(51) Int. Cl.
| | |
|---|---|
| *C07H 7/06* | (2006.01) |
| *C07H 19/052* | (2006.01) |
| *C07H 19/06* | (2006.01) |
| *C07H 19/23* | (2006.01) |

(52) U.S. Cl.
CPC ............... *C07H 19/23* (2013.01); *C07H 7/06* (2013.01); *C07H 19/052* (2013.01); *C07H 19/06* (2013.01)

(58) Field of Classification Search
None
See application file for complete search history.

(56) References Cited

U.S. PATENT DOCUMENTS 9,949,994 B2 * 4/2018 Chun ..................... A61K 31/00
2012/0263678 A1 * 10/2012 Cho ..................... A61K 31/351
424/85.4

* cited by examiner

*Primary Examiner* — Traviss C McIntosh, III
(74) *Attorney, Agent, or Firm* — Rumit Ranjit Kanakia

(57) ABSTRACT

The present application belongs to the field of chemical synthesis, and specifically relates to a six-membered ring-containing nucleoside compound and a preparation method thereof. The present application discloses a six-membered ring-containing nucleoside compound. The structural formula of the nucleoside compound 7 is:

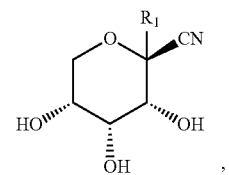

where $R_1$ is selected from one of

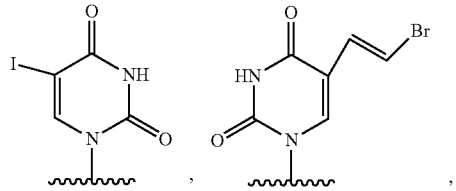

, and

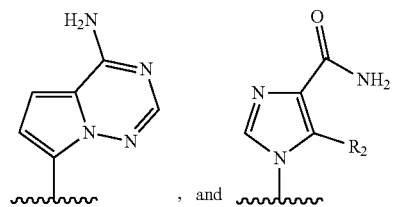

;

where $R_2$ is hydroxyl or alkynyl.

2 Claims, No Drawings

SIX-MEMBERED RING-CONTAINING NUCLEOSIDE COMPOUND AND PREPARATION METHOD THEREOF

TECHNICAL FIELD

The present application belongs to the field of chemical synthesis, and in particular to a six-membered ring-containing nucleoside compound and a preparation method thereof.

BACKGROUND

Originally, coronavirus can infect the respiratory and digestive tracts of animals and humans. Normally, it causes only mild symptoms of infection in healthy people with normal immunity. However, in the SARS epidemic at the beginning of this century, it caused 8096 infections and claimed 774 lives in 27 countries around the world. Ten years later, the Middle East Respiratory Syndrome caused by MERS brought pain to 1,728 patients and took 624 lives. Coronaviruses can be divided into four categories based on genome and structure. Among them, α and β coronaviruses only infect mammals, while γ and σ coronaviruses mainly infect songbirds. Both SARS and MERS belong to beta coronaviruses. At the beginning of 2020, a certain number of pneumonia caused by coronavirus broke out in Wuhan, China. These coronaviruses bring considerable pain to human and even directly threaten life. Up to now, people still haven't found effective methods and vaccines against coronaviruses. Therefore, the development of new drugs against coronaviruses is of great significance.

In the past 30 years of clinical treatment for SARS and MERS, there is still no effective treatment. The patients are mainly treated by combining ribavirin with various interferons, sometimes using lopinavir and ritonavir which are drugs used for treating HIV, and even using broad-spectrum antibiotics. In the research of various antiviral drugs, small molecule nucleoside (TEAD) antiviral drugs (such as favipiravir and brincidofovir) have entered clinical trials in recent years. In particular, a nucleoside analog, Galidesivir, has also entered clinical development. Unfortunately, none of these existing treatments can treat acute infections or persistent viral infections and their sequelae. Therefore, it is of great significance to develop convenient and effective drugs for treating coronavirus diseases.

In recent years, research on nucleoside antitumor and antiviral drugs has been extremely active. Up to now, several nucleoside antitumor drugs have entered the market. For anti-viral drugs, many patents and documents have been reported (see WO 2015/069939 A1; WO 2017/184668 A1; ES 2 465 265 T3; CN 102015714 A). In particular, in recent years, a class of monophosphate amide prodrugs with anti-ebola virus (ebov) activity, represented by GS-5734 (shown in formula I) and GS-441524 (shown in formula II) have found favor in the eyes of pharmaceutical chemists (Nature 2016, 531, 381-385; J. Med. Chem. 2017, 60, 1648-1661; Veterinary Microbiology 2018, 219, 226-233). Unfortunately, most of the studies on the molecule of these nucleoside drugs and analogs are focused on five-membered sugar rings, and the vast majority of these nucleoside drugs have a disadvantage that they are difficult to dissolve in neutral water and most organic solvents (only soluble in dimethyl sulfoxide and N,N-dimethylformamide), which has brought much trouble for further purification of clinical chemical drugs and injection dosage research. However, there is no literature reporting nucleoside drugs containing six-membered sugar rings or relevant research. From the perspective of pharmaceutical chemistry research, the chair-like conformation of the six-membered ring structure may exhibit different pharmacological activities in vivo. Therefore, it is necessary to develop a six-membered ring-contained nucleoside drug with better solubility and higher in vivo activity.

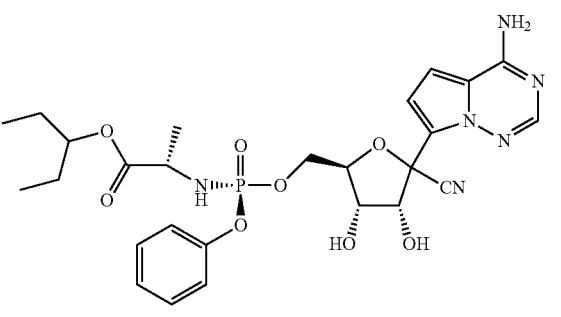

Formula I

GS-5734

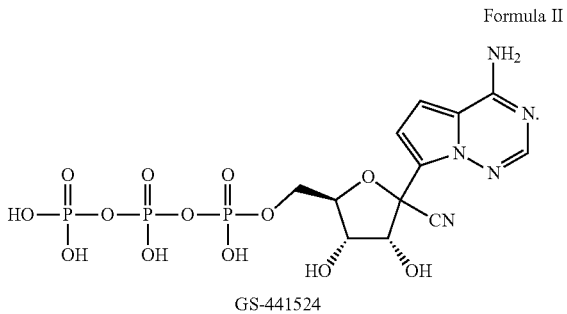

Formula II

GS-441524

SUMMARY

In order to solve the above technical problem, in a first aspect, the present application provides a nucleoside compound containing six-membered ring, wherein the structural formula of the nucleoside compound 7 is:

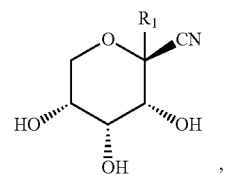

where $R_1$ is selected from one of

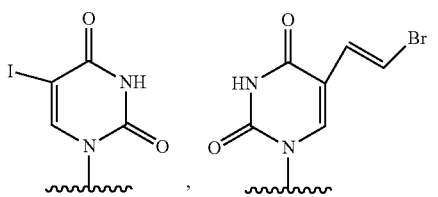

-continued

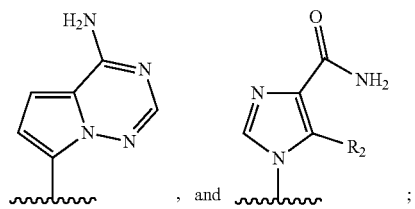 , and 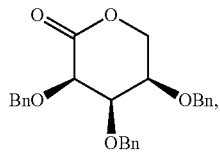 ;

and R$_2$ is hydroxy or alkynyl.

As a preferred technical solution, the structural formula of the six-membered ring-containing nucleoside compound 7 is

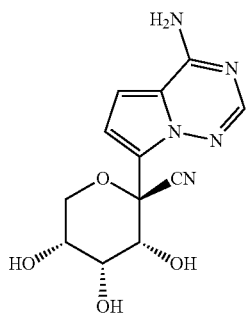

In a second aspect, the present application provides a method for preparing the nucleoside compound, comprising the following steps: compound 1 is dissolved in an organic solvent, BnX, an alkali metal halide, and an alkali metal salt excluding alkali metal halide are added thereto to react, and the reaction solution is post-treated to obtain compound 2, wherein the compound 1 is D-ribose and X is Br or Cl; the compound 2 is oxidized, substituted, cyanated, and debenzylated to obtain the nucleoside compound 7;

the structural formula of the compound 2 is:

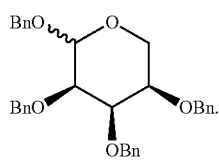 [SMILES: c1ccc(COC2OC[C@@H](OCc3ccccc3)[C@@H](OCc3ccccc3)[C@H]2OCc2ccccc2)cc1]

As a preferred technical solution, the preparation method comprises the following steps:

S1. compound 3 reacts with 7-iodopyrrolo[2,1-F][1,2,4]triazin-4-amine to obtain compound 4;

S2. the compound 4 reacts with Bronsted acid to obtain compound 5;

S3. Lewis acid and a cyanating agent are added to the compound 5, and the reaction solution is post-treated to obtain compound 6;

S4. the compound 6 is debenzylated to obtain the nucleoside compound 7;

the structural formula of the compound 3 is:

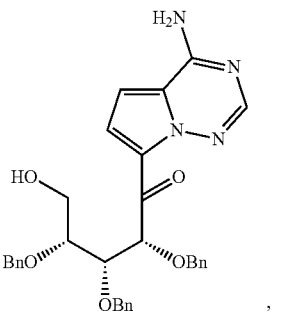 [SMILES: Nc1ncnn2c(C(=O)[C@H](OCc3ccccc3)[C@H](OCc3ccccc3)[C@@H](CO)OCc3ccccc3)ccc12]

the structural formula of the compound 4 is:

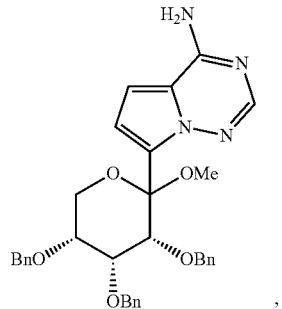 [SMILES: COC1(c2ccc3c(N)ncnn23)OC[C@@H](OCc2ccccc2)[C@@H](OCc2ccccc2)[C@H]1OCc1ccccc1]

the structural formula of the compound 5 is:

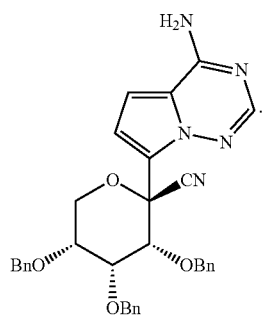 [SMILES: N#C[C@]1(c2ccc3c(N)ncnn23)OC[C@@H](OCc2ccccc2)[C@@H](OCc2ccccc2)[C@H]1OCc1ccccc1]

and the structural formula of the compound 6 is:

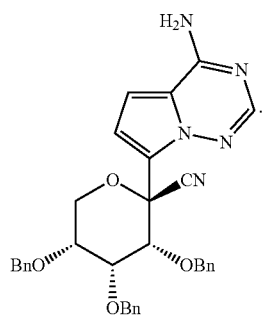 [SMILES: N#C[C@]1(c2ccc3c(N)ncnn23)OC[C@@H](OCc2ccccc2)[C@@H](OCc2ccccc2)[C@H]1OCc1ccccc1]

As a preferred technical solution, the method for preparing the compound 3 comprises the following steps: the compound 2 is prepared into a hemiacetal intermediate which then reacts with an oxidant for 3-12 hours to obtain the compound 3.

The structural formula of the compound 2 is:

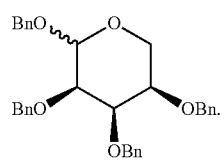

As a preferred technical solution, the method for preparing the compound 3 comprises the following steps: the compound 2 is dissolved in glacial acetic acid and stirred for 5-15 minutes, sulfuric acid and/or hydrochloric acid are added thereto, and then the system is heated to 70-90° C. to react for 4-6 h; after cooling, the system is adjusted to a pH of 3.8-4.2 with 0.5-1.5 M sodium hydroxide, concentrated under reduced pressure to remove glacial acetic acid, and then extracted; the organic phases are combined, washed, dried, and then filtered to obtain a filtrate; the filtrate is concentrated, and subjected to column chromatography to obtain the hemiacetal intermediate; the hemiacetal intermediate is dissolved in dry dichloromethane, an oxidant is added thereto to react for 3-12 hours, and the reaction solution is quenched and extracted; the organic phases are combined, washed and dried, and then filtered to obtain a filtrate; the filtrate is concentrated and subjected to column chromatography to obtain the compound 3.

As a preferred technical solution, the oxidant is at least one selected from the group consisting of pyridinium chlorochromate, pyridine dichromate, Dess-Martin oxidant, and DMSO/(COCl)$_2$.

As a preferred technical solution, the step S comprises: 7-iodopyrrolo[2,1-F][1,2,4]triazin-4-amine is dissolved in dry tetrahydrofuran, halogenated silane or estersil is added thereto, phenyl magnesium halide is added thereto after stirring for 5-15 minutes, and alkyl magnesium halide is added thereto after stirring for 15-25 minutes to further react for 15-25 minutes, and then a solution of the compound 3 in tetrahydrofuran is added thereto; after 5.5-6.5 hours of reaction, the reaction solution is quenched, and extracted, organic phases are combined, washed, dried and filtered; the filtrate is concentrated and subjected to column chromatography to obtain the compound 4; preferably, the halogenated silane is at least one selected from the group consisting of trimethylchlorosilane, trimethyliodosilane, trimethylbromosilane, and triethylchlorosilane; and the estersil is at least one selected from the group consisting of trimethylsilyl trifluoromethanesulfonate, and trimethysilyl 1 perchlorate.

As a preferred technical solution, in the step S2, the Bronsted acid is at least one selected from the group consisting of camphorsulfonic acid, p-toluenesulfonic acid, p-toluenesulfonic acid monohydrate, benzenesulfonic acid, methanesulfonic acid, benzenesulfonic acid, and fumaric acid.

As a preferred technical solution, in the step S3, the Lewis acid is at least one selected from the group consisting of trimethylchlorosilane, trimethyliodosilane, trimethylbromosilane, triethylchlorosilane, trimethylsilyl trifluoromethanesulfonate, trimethylsilyl perchlorate, and boron trifluoride diethyl etherate.

Beneficial effects: The preparation method of the six-membered ring-containing nucleoside compound described in this application features simple technical route and simple operation, and all the agents used in this method are common agents. It is suitable for large-scale production and can easily achieve production of 10-100 g level in the laboratory.

DETAILED DESCRIPTION OF EMBODIMENTS

In order to solve the above problem, the present application provides a six-membered ring-containing nucleoside compound. The structural formula of the nucleoside compound 7 is:

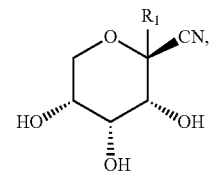

where $R_1$ is selected from one of

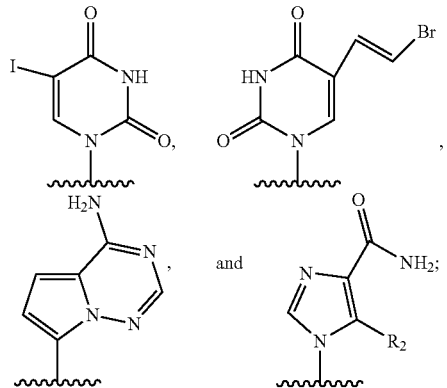

and $R_2$ is hydroxy or alkynyl.

The $R_1$ group plays a decisive role in the antiviral spectrum of nucleosides and nucleoside derivatives. When the nucleoside compound obtained by changing the $R_1$ group is inserted into the DNA or RNA chain, the biological genetic material changes, thereby Interfering with the synthesis of viruses; and the substituents on the $R_1$ group should not be too large, or the nucleoside compound would have no activity.

As a preferred embodiment, the structural formula of the six-membered ring-containing nucleoside compound 7 is

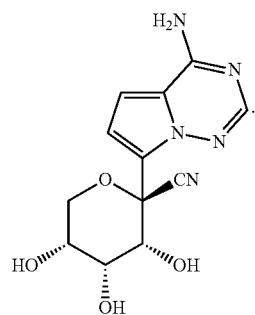

The six-membered ring-containing nucleoside compounds 7 according to the present application are similar in chemical structure to natural nucleosides, and can act just like the natural ones in the body, thereby interfering or directly acting on the biosynthesis of proteins and nucleic acids to interfere with the synthesis of viruses, especially coronaviruses. Additionally, the nucleoside compound 7 contains a six-membered ring, which has good solubility and higher activity in the body.

The preparation method of the nucleoside compound includes the following steps: compound 1 is dissolved in an organic solvent, BnX, an alkali metal halide, and an alkali metal salt excluding alkali metal halide are added thereto to react, and the reaction solution is post-treated to obtain compound 2, wherein the compound 1 is D-ribose and X is Br or Cl; the compound 2 is oxidized, substituted, cyanated, and debenzylated to obtain the nucleoside compound 7; the structural formula of the compound 2 is:

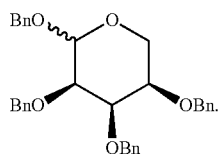 [SMILES: c1ccc(COC2OC[C@@H](OCc3ccccc3)[C@@H](OCc3ccccc3)[C@H]2OCc2ccccc2)cc1]

As a preferred embodiment, the preparation method of the six-membered ring-containing nucleoside compound 7 includes the following steps:

S1. compound 3 reacts with 7-iodopyrrolo[2,1-F][1,2,4]triazin-4-amine to obtain compound 4;
S2. the compound 4 reacts with Bronsted acid to obtain compound 5;
S3. Lewis acid and a cyanating agent are added to the compound 5, and the reaction solution is post-treated to obtain compound 6;
S4. the compound 6 is debenzylated to obtain the nucleoside compound 7;
the structural formula of the compound 4 is:

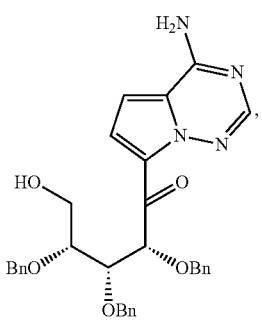 [SMILES: Nc1ncnn2c(C(=O)[C@H](OCc3ccccc3)[C@H](OCc3ccccc3)[C@@H](CO)OCc3ccccc3)ccc12]

the structural formula of the compound 5 is:

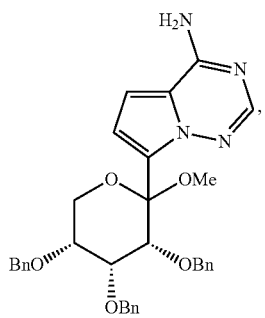 [SMILES: COC1(c2ccc3c(N)ncnn23)OC[C@@H](OCc2ccccc2)[C@@H](OCc2ccccc2)[C@H]1OCc1ccccc1]

and the structural formula of the compound 6 is:

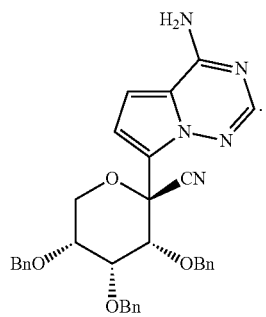 [SMILES: N#C[C@]1(c2ccc3c(N)ncnn23)OC[C@@H](OCc2ccccc2)[C@@H](OCc2ccccc2)[C@H]1OCc1ccccc1]

Step S1

As an embodiment, the method for preparing compound 3 comprises the following steps: compound 2 is prepared into a hemiacetal intermediate, and then reacts with an oxidant for 3-12 hours to obtain compound 3;

The oxidant may be added in any suitable amount; preferably, the amount of substance of the oxidant is 1-2 times that of the compound 2.

Among others, the oxidant is at least one selected from the group consisting of pyridinium chlorochromate, pyridine dichromate, Dess-Martin oxidant, and DMSO/(COCl)$_2$.

The structural formula of the compound 2 is

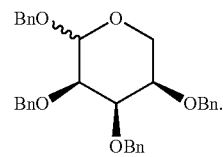

The structural formula of the compound 3 is:

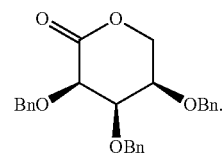

The pyridinium chlorochromate is abbreviated as PCC, with CAS No. 26299-14-9, and can oxidize hydroxyl group to aldehyde group under neutral conditions at room temperature.

The pyridine dichromate is referred to as PDC for short, with CAS No. 20039-37-6.

The Dess-Martin oxidant is abbreviated as DMP, with CAS No. 87413-09-0, and can oxidize primary alcohol to aldehyde and secondary alcohol to ketone.

Preferably, the method for preparing the compound 3 comprises the following steps: the compound 2 is dissolved in glacial acetic acid and stirred for 5-15 minutes, sulfuric acid and/or hydrochloric acid are added thereto, and then the system is heated to 70-90° C. to react for 4-6 h; after cooling, the system is adjusted to a pH of 3.8-4.2 with 0.5-1.5 M sodium hydroxide, concentrated under reduced pressure to remove glacial acetic acid, and then extracted; organic phases are combined, washed, dried and then filtered to obtain a filtrate; the filtrate is concentrated, and subjected to column chromatography to obtain a hemiacetal intermediate; the hemiacetal intermediate is dissolved in dry dichloromethane, an oxidant is added thereto to react for 3-12 hours, and the reaction solution is quenched, and extracted; the organic phases are combined, washed and dried, and then filtered to obtain a filtrate; the filtrate is concentrated and subjected to column chromatography to obtain the compound 3.

Preferably, the method for preparing the compound 3 comprises the following steps: the compound 2 is dissolved in glacial acetic acid and stirred for 5-15 minutes, sulfuric acid and/or hydrochloric acid are added thereto, and then the system is heated to 70-90° C. to react for 4-6 h; after cooling, the system is adjusted to a pH of 3.8-4.2 with 0.5-1.5 M sodium hydroxide, concentrated under reduced pressure to remove glacial acetic acid, and then extracted with ethyl acetate; the organic phases are combined, washed with saturated sodium chloride, dried over anhydrous magnesium sulfate, and then filtered to obtain a filtrate; the filtrate is concentrated, and subjected to column chromatography to obtain a hemiacetal intermediate; the hemiacetal intermediate is dissolved in dry dichloromethane, an oxidant is added thereto to react for 3-12 hours, and the reaction solution is quenched, and extracted with dichloromethane; the organic phases are combined, washed with saturated sodium chloride, dried over anhydrous magnesium sulfate, and then filtered to obtain a filtrate; the filtrate is concentrated and subjected to column chromatography to obtain the compound 3.

As an embodiment, the method for preparing the compound 2 comprises the following steps: the compound 1 is dissolved in an organic solvent, BnX (X is Br or C), an alkali metal halide, and an alkali metal salt excluding alkali metal halide are added thereto to react, and the reaction solution is post-treated to obtain the compound 2.

The compound 1 is D-ribose, with a structural formula of:

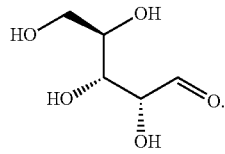

BnX can be added in any suitable amount; preferably, the amount of substance of the BnX is 4-5 times that of the compound 1.

The alkali metal halide may be added in any suitable amount; preferably, the amount of substance of the alkali metal halide is 0.02-0.06 times that of the compound 1.

The alkali metal salt excluding alkali metal halide may be added in any suitable amount; preferably, the amount of substance of the alkali metal salt excluding alkali metal halide is 3-6 times that of the compound 1.

The organic solvent is at least one selected from the group consisting of dichloromethane, tetrahydrofuran, dimethyl sulfoxide, acetonitrile, toluene, and N,N-dimethylformamide.

When X is Br, the BnX refers to $PhCH_2Br$; when X is C, the BnX refers to $PhCH_2$ Cl.

The alkali metal halide is at least one selected from the group consisting of sodium iodide, potassium iodide, sodium bromide, potassium bromide, sodium chloride, and potassium chloride.

The alkali metal salt excluding alkali metal halide is at least one selected from the group consisting of potassium carbonate, sodium carbonate, potassium t-butoxide, sodium hydride, lithium diisopropylamide, and n-butyl lithium.

Preferably, the method for preparing the compound 2 comprises the following steps: the compound 1 is dissolved in an organic solvent, BnX (X is Br or Cl) and an alkali metal halide are added thereto; then an alkali metal salt excluding alkali metal halide is added thereto to react at a temperature controlled at 30-35° C. for 5-12 h; thereafter, the reaction solution is quenched with water, and extracted; the organic phases are combined, washed, dried and then filtered to obtain a filtrate; the filtrate is concentrated and subjected to column chromatography to obtain the compound 2.

More preferably, the method for preparing the compound 2 comprises the following steps: the compound 1 is dissolved in an organic solvent, BnX (X is Br or Cl) and an alkali metal halide are added thereto; then an alkali metal salt excluding alkali metal halide is added thereto in portions to react at a temperature controlled at 30-35° C. for 5-12 h; thereafter, the reaction solution is quenched with water, and extracted three times with ethyl acetate; the organic phases are combined and washed twice with water, once with saturated sodium chloride, dried over anhydrous magnesium sulfate, and then filtered to obtain a filtrate; the filtrate is concentrated and subjected to column chromatography to give the compound 2. Among others, the alkali metal salt excluding alkali metal halide may be added in any suitable number of batches, for example, the alkali metal salt excluding alkali metal halide is added in 2 batches; or the alkali metal salt excluding alkali metal halide is added in 3 batches; or the alkali metal salt excluding alkali metal halide is added in 4 batches.

As a preferred embodiment, the step S1 comprises: 7-iodopyrrolo[2,1-F][1,2,4]triazin-4-amine is dissolved in dry tetrahydrofuran, halogenated silane or estersil is added thereto, phenyl magnesium halide is added thereto after stirring for 5-15 minutes, alkyl magnesium halide is added thereto after stirring for 15-25 minutes to further react for 15-25 minutes, and then a solution of the compound 3 in tetrahydrofuran is added thereto; after 5.5-6.5 hours of reaction, the reaction solution is quenched, and extracted, the organic phases are combined, washed, dried and filtered; the filtrate is concentrated and subjected to column chromatography to obtain the compound 4.

7-iodopyrrolo[2,1-F][1,2,4]triazin-4-amine can be added in any suitable amount; preferably, the amount of substance of the 7-iodopyrrolo[2,1-F][1,2,4]triazin-4-amine is 0.8-1.1 times that of the compound 3.

The CAS number of 7-iodopyrrolo[2,1-F][1,2,4]triazine-4-amine is 1770840-43-1.

The halogenated silane is at least one selected from the group consisting of trimethylchlorosilane, trimethyliodosilane, trimethylbromosilane, and triethylchlorosilane; and the estersil is at least one selected from the group consisting of trimethylsilyl trifluoromethanesulfonate, and trimethysilyl I perchlorate.

The phenyl magnesium halide is phenyl magnesium chloride.

The alkyl magnesium halide is at least one selected from the group consisting of isopropyl magnesium chloride, tert-butyl magnesium chloride, methyl magnesium chloride, ethyl magnesium bromide, ethyl magnesium chloride, propyl magnesium bromide, and propyl magnesium chloride.

More preferably, the step S1 comprises: 7-iodopyrrolo[2,1-F][1,2,4]triazin-4-amine is dissolved in dry tetrahydrofuran, halogenated silane or estersil is added thereto, phenyl magnesium halide is added thereto after stirring for 5-15 minutes, alkyl magnesium halide is added thereto after stirring for 15-25 minutes to further react for 15-25 minutes, and then a solution of the compound 3 in tetrahydrofuran is added thereto; after 6 hours of reaction, the reaction solution is quenched with saturated ammonium chloride, and extracted with ethyl acetate; the organic phases are combined, washed with saturated sodium chloride and dried over anhydrous magnesium sulfate, and then filtered to obtain a filtrate; the filtrate is concentrated and subjected to column chromatography to obtain the compound 4.

Step S2

The Bronsted acid is a sulfonic acid compound and/or a carboxylic acid compound; preferably, the Bronsted acid is at least one selected from the group consisting of camphorsulfonic acid, p-toluenesulfonic acid, p-toluenesulfonic acid monohydrate, benzenesulfonic acid, methanesulfonic acid, benzenesulfonic acid, and fumaric acid.

Preferably, the step S2 comprises: the compound 4 is dissolved in methanol, Bronsted acid is added thereto, and the reaction solution is stirred overnight; methanol is removed, a saturated sodium bicarbonate solution is added thereto, and the reaction solution is extracted with ethyl acetate; the organic phases are combined, washed, dried and then filtered to obtain a filtrate; the filtrate is concentrated and subjected to column chromatography to obtain the compound 5.

The method of removing methanol is not particularly limited, and can be, for example, distillation under reduced pressure.

The Bronsted acid may be added in any suitable amount; preferably, the amount of the substance of the Bronsted acid is 2-3 times that of the compound 4.

More preferably, the step S2 comprises: the compound 4 is dissolved in methanol, Bronsted acid is added thereto, and the reaction solution is stirred overnight; methanol is removed, a saturated sodium bicarbonate solution is added thereto, and the reaction solution is extracted with ethyl acetate; the organic phases are combined, washed with saturated sodium chloride and dried over anhydrous magnesium sulfate, and then filtered to obtain a filtrate; the filtrate was concentrated and subjected to column chromatography to give compound 5.

Step S3

The Lewis acid is at least one selected from the group consisting of trimethylchlorosilane, trimethyliodosilane, trimethylbromosilane, triethylchlorosilane, trimethylsilyl trifluoromethanesulfonate, trimethylsilyl perchlorate, and boron trifluoride diethyl etherate.

The cyanating agent is at least one selected from the group consisting of trimethylcyanosilane, tetrabutylammonium cyanide, tetramethylammonium cyanide, tetraethylammonium cyanide, sodium cyanide, and potassium cyanide.

The Lewis acid can be added in any suitable amount; preferably, the amount of substance of the Lewis acid is 2-4 times that of the compound 5.

The cyanating agent may be added in any suitable amount; preferably, the amount of the substance of the cyanating agent is 4-5 times that of the compound 5.

As a preferred embodiment, the step S3 comprises: the compound 5 is dissolved in dry dichloromethane, placed in an ice salt bath, Lewis acid is added thereto, and a cyanating agent is added thereto after stirring for 25-35 minutes; the reaction solution is allowed to warm naturally to room temperature over a certain period of time, and then quenched, and extracted; the organic phases are combined, washed and dried, and then filtered to obtain a filtrate; the filtrate is concentrated and subjected to column chromatography to obtain the compound 6.

Further preferably, the step S3 comprises: the compound 5 is dissolved in dry dichloromethane, placed in an ice salt bath, Lewis acid is added thereto, and a cyanating agent is added thereto after stirring for 25-35 minutes; the reaction solution is allowed to warm naturally to room temperature over a certain period of time, and then quenched with saturated sodium bicarbonate, and extracted with dichloromethane; the organic phases are combined, washed with saturated sodium chloride and dried over anhydrous magnesium sulfate, and then filtered to obtain a filtrate; the filtrate is concentrated and subjected to column chromatography to obtain the compound 6.

Step S4

The compound 6 is dissolved in dry dichloromethane, cooled down to $-(70-80°)$ C, a debenzylating agent is added thereto, and the reaction solution is heated to $-(35-45°)$ C to react for 7-9 h; C1-C2 organic alcohol is added thereto, a mixed solution of an alkali and the C1-C2 organic alcohol is further added thereto, and the system is warmed to room temperature; the solvent is distilled off under reduced pressure to obtain a crude product, which is washed with an organic compound to obtain the nucleoside compound 7.

The debenzylating agent is at least one selected from the group consisting of boron trichloride, boron trifluoride, boron tribromide, ferric chloride, aluminum trichloride, titanium tetrachloride, and tin tetrachloride.

The alkali is at least one selected from the group consisting of sodium hydroxide, potassium hydroxide, triethylamine, diethylamine, sodium carbonate, and potassium carbonate.

The C1-C2 organic alcohol is methanol and/or ethanol.

The organic compound is at least one selected from the group consisting of dichloromethane, tetrahydrofuran, acetonitrile, and chloroform.

In this application, the drying method is not particularly limited, and for example, anhydrous calcium chloride, and anhydrous sodium carbonate may also be used.

The preparation method of the nucleoside compound 7 of the present application features simple technical route and simple operation, and all the agents used in this method are common agents. It is suitable for large-scale production and can easily achieve production of 10-100 g level in the laboratory.

In this application, stirring overnight means stirring for 10-14 hours.

The present application will be described in detail below through examples. It is necessary to point out here that the following examples are only used to further illustrate the present application and cannot be understood as a limitation to the protection scope of the present application. Some non-essential improvements and adjustments made by those skilled in the art based on the content of the present application described above are still within the protection scope of the present application.

In addition, unless otherwise stated, the raw materials used are all commercially available.

EXAMPLES

Example 1

A method for preparing a six-membered ring-containing nucleoside compound 7, comprising the following steps:

S1. The preparation method of compound 2, comprising the following steps: D-ribose (compound 1) (10 g, 66.6 mmol) was dissolved in 300 mL of N,N-dimethylformamide, and benzyl bromide (36 mL, 299.7 mmol) and potassium iodide (445 mg, 2.7 mmol) were added thereto. Sodium hydride (13.4 g, 333 mmol, 60% in oil) was added in 4 equal portions, and the reaction temperature was controlled between 30° C. and 35° C. After 12 hours, the reaction solution was quenched with water, and extracted three times with ethyl acetate. The combined organic phases were washed twice with water and once with saturated sodium chloride, dried over anhydrous magnesium sulfate, and then filtered to obtain a filtrate. The filtrate was concentrated and subjected to column chromatography to give compound 2 of 14.6 g, with a yield of 43%.

The compound 2 (9.3 g, 18.2 mmol) was dissolved in 120 mL of glacial acetic acid, stirred for 10 minutes, dilute sulfuric acid (37 mL, 1 M in $H_2O$) was added thereto, and then the system was heated to 80° C. to react for 5 hours. After cooling, the reaction solution was adjusted to pH 4 with 1 M sodium hydroxide, concentrated under reduced pressure to remove glacial acetic acid, and then extracted three times with ethyl acetate. The combined organic phases were washed once with saturated sodium chloride, dried over anhydrous magnesium sulfate, and then filtered to obtain a filtrate. The filtrate was concentrated and subjected to column chromatography to obtain a hemiacetal intermediate (the mass of the hemiacetal intermediate is 5.8 g, and the yield is 76%). This intermediate (5.1 g, 12.1 mmol) was dissolved in 50 mL of dry methylene chloride, and DMP oxidant (10.3 g, 24.2 mmol) was added thereto to react for 3 hours. The reaction solution was quenched with saturated sodium bicarbonate and sodium thiosulfate solids and extracted three times with dichloromethane. The combined organic phases were washed once with saturated sodium chloride, dried over anhydrous magnesium sulfate, and then filtered to obtain a filtrate. The filtrate was concentrated and subjected to column chromatography to obtain compound 3 (the mass of the compound 3 is 4.7 g, and the yield is 92%). 1H NMR (400 MHz, $CDCl_3$) δ:7.45-7.42 (m, 2H), 7.41-7.38 (m, 5H), 7.38-7.35 (m, 3H), 7.35-7.31 (m, 3H), 7.30-7.28 (m, 2H), 5.12 (d, J=8.0 Hz, 1H), 4.99 (d, J=8.0 Hz, 1H), 4.91 (d, J=8.0 Hz, 1H), 4.71 (d, J=8.0 Hz, 1H), 4.56 (d, J=8.0 Hz, 1H), 4.51-4.45 (m, 2H), 4.32-4.29 (m, 1H), 4.27-4.26 (m, 1H), 3.88 (d, J=1.6 Hz, 1H), 3.83 (ddd, J=6.8, 4.0, 1.2 Hz, 1H) ppm;

Compound 7-iodopyrrolo[2,1-F][1,2,4]triazin-4-amine (15 g, 57.7 mmol) was dissolved in 350 mL of dry tetrahydrofuran, and trimethylchlorosilane (14.6 mL, 115.4 mmol) was added thereto. After stirring for 10 minutes, the system was cooled down to 0° C., and phenylmagnesium chloride (58 mL, 2.0 M in THF) was added thereto. After stirring for 20 minutes, isopropyl magnesium chloride (47 mL, 1.3 M in THF) was added thereto. After the reaction continued for 20 minutes, 100 mL of a solution of the compound 3 (24.5 g, 58.6 mmol) in tetrahydrofuran was added dropwise within 20 minutes. After 6 hours of reaction at this temperature, the reaction solution was quenched with saturated ammonium chloride, and extracted three times with ethyl acetate. The organic phases were combined, washed once with saturated sodium chloride, dried over anhydrous magnesium sulfate, and then filtered to obtain a filtrate. The filtrate was concentrated and subjected to column chromatography to obtain compound 4 (the mass of the compound 4 is 16.8 g, the yield is 52%). 1H NMR (400 MHz, DMSO) δ: 8.08 (brs, 2H), 8.03 (s, 1H), 7.38-7.35 (m, 2H), 7.32-7.27 (m, 7H), 7.26-7.20 (m, 5H), 7.16-7.13 (m, 2H), 6.94 (d, J=3.2 Hz, 1H), 5.53 (d, J=3.2 Hz, 1H), 4.69 (d, J=8.0 Hz, 1H), 4.62 (s, 2H), 4.59-4.55 (m, 2H), 4.52 (d, J=8.0 Hz, 1H), 4.50 (d, J=7.6 Hz, 1H), 4.13-4.10 (m, 1H), 3.85-3.81 (m, 1H), 3.80-3.76 (m, 1H), 3.62-3.57 (m, 1H) ppm.

S2. The compound 4 (32 g, 59.4 mmol) was dissolved in 300 mL of methanol, p-toluenesulfonic acid monohydrate (28.2 g, 148.5 mmol, CAS No. 6192-52-5) was added thereto. After reaction with stirring for 12 hours, methanol was distilled off under reduced pressure. A saturated sodium bicarbonate solution was added thereto, and the reaction solution was extracted three times with ethyl acetate. The organic phases were combined, washed once with saturated sodium chloride, dried over anhydrous magnesium sulfate, and then filtered to obtain a filtrate. The filtrate was concentrated and subjected to column chromatography to obtain compound 5 (the mass of compound 5 is 28 g, the yield is 85%). 1H NMR (400 MHz, CDCl3) δ: 7.78 (s, 1H), 7.42-7.38 (m, 2H), 7.37-7.28 (m, 5H), 7.27-7.20 (m, 3H), 7.09-7.02 (m, 2H), 7.00-6.94 (m, 2H), 6.74 (d, J=7.2 Hz, 1H), 6.62 (d, J=4.4 Hz, 1H), 5.73 (s, 2H), 4.92 (d, J=12.8 Hz, 1H), 4.84-4.78 (m, 2H), 4.64-4.52 (m, 3H), 4.37 (d, J=12.0 Hz, 1H), 4.17-4.14 (m, 1H), 4.11 (d, J=12.4 Hz, 1H), 3.88-3.81 (m, 2H), 2.93 (s, 3H) ppm.

S3. The compound 5 (28 g, 49.5 mmol) was dissolved in 200 mL of dry dichloromethane, placed in an ice salt bath, and trimethylsilyl trifluoromethanesulfonate (28.7 mL, 148.5 mmol) was added thereto. After stirring for 30 minutes, trimethylcyanosilane (29.7 mL, 222.8 mmol) was added thereto, and the reaction solution was allowed to naturally warm to room temperature to react with stirring for 12 hours. The reaction solution was quenched with saturated sodium bicarbonate, and extracted three times with dichloromethane. The organic phases were combined, washed once with saturated sodium chloride, dried over anhydrous magnesium sulfate, and then filtered to obtain a filtrate. The filtrate was concentrated and subjected to column chromatography to give compound 6 (the mass of compound 6 is 25.5 g, and the yield is 92%). 1H NMR (400 MHz, $CDCl_3$) δ: 7.82 (s, 1H), 7.40-7.30 (m, 7H), 7.27-7.20 (m, 4H), 7.10-7.05 (m, 1H), 7.01-6.94 (m, 3H), 6.77-6.72 (m, 2H), 6.64-6.59 (m, 1H), 5.92 (brs, 2H), 5.00 (s, 1H), 4.88 (d, J=12.4 Hz, 1H), 4.79 (d, J=12.4 Hz, 1H), 4.63-4.58 (m, 2H), 4.45 (d, J=11.6 Hz, 1H), 4.39 (d, J=13.6 Hz, 1H), 4.24 (d, J=12.0 Hz, 1H), 4.20-4.14 (m, 2H), 3.95-3.90 (m, 1H) ppm.

S5. The compound 6 (34.8 g, 62.0 mmol) was dissolved in 250 mL of dry dichloromethane, cooled down to −78° C., boron trichloride (236 mL, 1 M in DCM) was added thereto, and the mixture was warmed to −40° C. to react for 8 hours. 120 mL of anhydrous methanol was added thereto, and then a mixed solution of triethylamine (87 mL) and anhydrous methanol (120 mL) was further added thereto. Then, the system was warmed to room temperature, the solvent was distilled off under reduced pressure to obtain a crude product, which was washed with chloroform four times to give nucleoside compound 7 (the mass of the nucleoside compound 7 is 15.3 g, and the yield is 85%). 1H NMR (400 MHz, DMSO) δ: 7.84 (s, 1H), 7.76 (brs, 2H), 6.83 (d, J=4.4 Hz, 1H), 6.63 (d, J=4.4 Hz, 1H), 5.60 (d, J=5.2 Hz, 1H), 5.34 (d, J=4.8 Hz, 1H), 5.02 (d, J=8.8 Hz, 1H), 4.67 (d, J=8.8 Hz, 1H), 4.08 (d, J=12.8 Hz, 1H), 3.98 (d, J=12.8 Hz, 1H), 3.86-3.81 (m, 2H) ppm.

In the above, THF refers to tetrahydrofuran; DCM refers to dichloromethane.

2.0 M in THF means that the concentration of phenyl magnesium chloride in THF is 2.0 mol/L.

Example 2

A method for preparing a six-membered ring-containing nucleoside compound 7, the specific steps of which are the same as in Example 1, except for the following points:

Compound 2 (9.3 g, 18.2 mmol) was dissolved in 120 mL of glacial acetic acid, stirred for 10 minutes, dilute hydrochloric acid (37 mL, 1 M in $H_2O$) was added thereto, and then the system was heated to 80° C. to react for 5 hours. After cooling, the reaction solution was adjusted to pH 4 with 1 M sodium hydroxide, concentrated under reduced pressure to remove glacial acetic acid, and then extracted three times with ethyl acetate. The combined organic phases were washed once with saturated sodium chloride, dried over anhydrous magnesium sulfate, and then filtered to obtain a filtrate. The filtrate was concentrated and subjected to column chromatography to obtain a hemiacetal intermediate (5.8 g, 76%). This intermediate (5.1 g, 12.1 mmol) was dissolved in 50 mL of dry methylene chloride, and pyridinium chlorochromate (PCC oxidant) (5.2 g, 24.2 mmol) was added thereto to react for 3 hours. The reaction solution was quenched with saturated sodium bicarbonate and sodium thiosulfate solids, and extracted three times with dichloromethane. The combined organic phases were washed once with saturated sodium chloride, dried over anhydrous magnesium sulfate, and then filtered to obtain a filtrate. The filtrate was concentrated and subjected to column chromatography to obtain compound 3 (the mass of the compound 3 is 4.0 g, and the yield is 80%).

Example 3

A method for preparing a six-membered ring-containing nucleoside compound 7, the specific steps of which are the same as in Example 1, except for the following points:

S3. Compound 5 (5 g, 8.8 mmol) was dissolved in 40 mL of dry dichloromethane, placed in an ice-salt bath, boron trifluoride etherate (3.3 mL, 26.5 mmol) was added thereto, and after stirring for 30 minutes, trimethyl cyanosilane (5.3 mL, 39.6 mmol) was added thereto, and the mixture was warmed to room temperature to react for 12 hours. The reaction solution was quenched with saturated sodium bicarbonate, and extracted three times with dichloromethane. The organic phases were combined, washed once with saturated sodium chloride, dried over anhydrous magnesium sulfate, and then filtered to obtain a filtrate. The filtrate was concentrated and subjected to column chromatography to give Compound 6 (the mass of the compound 6 is 2.7 g, and the yield is 54%).

The above are only preferred embodiments of the present application, and are not intended to limit the present application in other ways. Any person skilled in the art may use the technical content disclosed above to change or alter them to equivalent embodiments. However, any simple modification, equivalent change and modification made to the above embodiments based on the technical essence of the present application without departing from the technical solution of the present application still fall within the protection scope of the technical solution of the present application.

What is claimed is:

1. A six-membered ring-containing nucleoside compound, which is nucleoside compound 7 having the structural formula of:

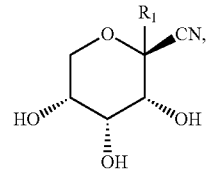

where R1 is selected from the group consisting of

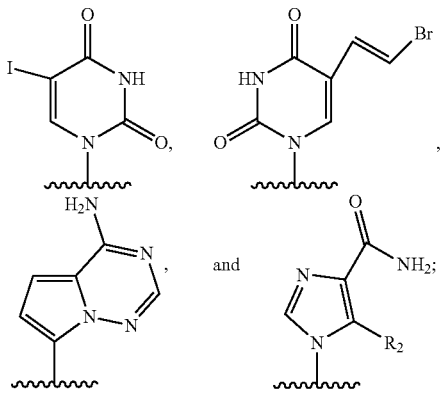

and R2 is hydroxy or alkynyl.

2. The six-membered ring-containing nucleoside compound according to claim 1, wherein the nucleoside compound 7 is

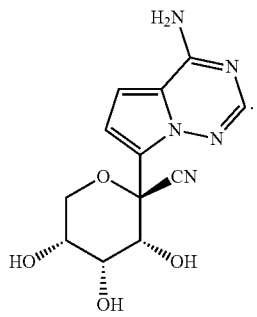 [SMILES: N#C[C@]1(c2ccc3c(N)ncnn23)OC[C@@H](O)[C@@H](O)[C@H]1O]

* * * * *